United States Patent [19]
Smith

[11] Patent Number: 5,399,151
[45] Date of Patent: Mar. 21, 1995

[54] LIFTING BELT AND METHOD

[75] Inventor: Neil Smith, Boca Raton, Fla.

[73] Assignee: FLA Orthopedics, Inc., Miami Lakes, Fla.

[21] Appl. No.: 118,889

[22] Filed: Sep. 10, 1993

[51] Int. Cl.6 ............................................. A61F 5/02
[52] U.S. Cl. ........................................ 602/19; 602/5; 2/44; 2/45
[58] Field of Search ............... 602/19, 20, 5, 61; 128/99.1, 101.1, 100.1; 2/44, 45, 92

[56] References Cited

U.S. PATENT DOCUMENTS

| | | | |
|---|---|---|---|
| 3,441,027 | 4/1969 | Lehman | 602/19 X |
| 5,148,549 | 9/1992 | Sydor | 602/19 X |
| 5,176,131 | 1/1993 | Votel et al. | 602/19 |
| 5,257,419 | 11/1993 | Alexander | 2/44 |

FOREIGN PATENT DOCUMENTS

981538  1/1965  United Kingdom ............. 128/100.1

Primary Examiner—Richard J. Apley
Assistant Examiner—Beverly A. Meindl
Attorney, Agent, or Firm—Jack E. Dominik

[57] ABSTRACT

A unisize type lifting belt containing basically three elements: the underlying wrap assembly with expandable back panel and overlapping closure ends; suspenders with four adjustable ends to secure to the underlying wrap assembly at varying positions in front and at two positions varying vertically in the rear; and expandable side pull portions which have a pair of elastic band portions and removably secured end tabs is disclosed. The expandable side pulls are normally applied by snugly securing the side pulls to the underlying wrap assembly prior to lifting.

8 Claims, 4 Drawing Sheets

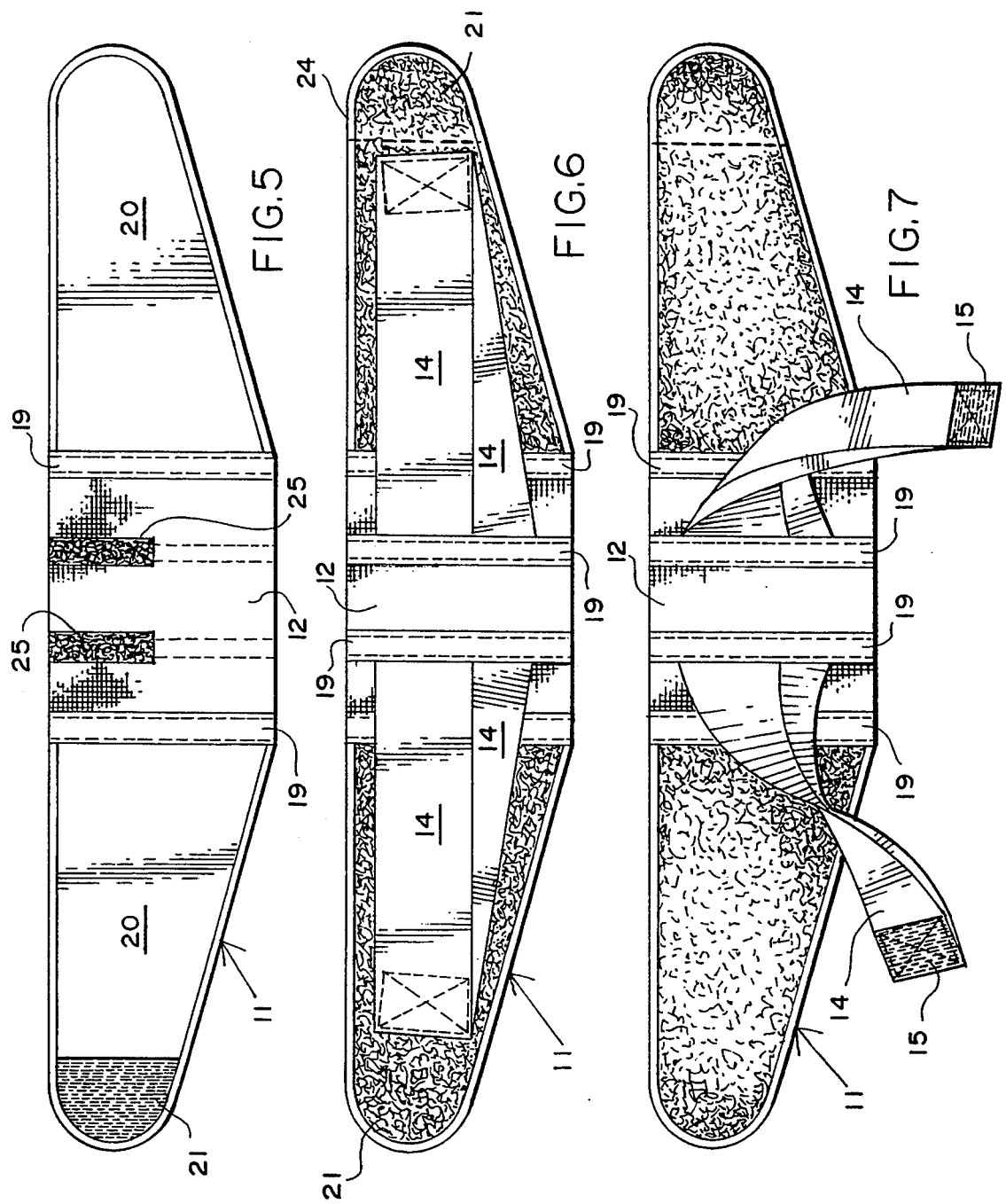

LIFTING BELT AND METHOD

FIELD OF THE INVENTION

The present invention relates to lifting belts, and more particularly the type used by do-it-yourselfers and industry employees who from-time-to-time are required to lift loads which could cause back injuries.

BACKGROUND OF THE INVENTION

The present invention is related to the field of lifting belts. Many sizes and varieties of lifting belts have been proposed and made and patented. Exemplary of such patented belts are U.S. Pat. Nos. 5,147,261; 4,907,576; and 4,964,401. While these lifting belts may serve the purpose of reducing back injuries, all of them are specially sized, which requires the marketer and manufacturer to make a minimum of four sizes: small, medium, large, and extra large.

SUMMARY OF THE INVENTION

The present invention is directed to unisize type lifting belt containing basically three elements: the underlying wrap assembly with expandable back panel and overlapping closure ends; suspenders with four adjustable ends to secure to the underlying wrap assembly at varying positions in front and at two positions varying vertically in the rear; and expandable side pull portions which have a pair of elastic band portions and removably secured end tabs. The expandable side pulls are normally applied by snugly securing the side pulls to the underlying wrap assembly prior to lifting.

The principal object of the present invention is to provide a load belt which can readily adapt from a slender person to a large person from one particular size belt. Such persons may vary substantially in both girth and height as well as weight.

Yet another advantage of the present lifting belt is a structure which is inherently inexpensive to manufacture and cost efficient as well as cost effective for the end use.

A further advantage of the present invention is to provide a method for securing a properly adapted lifting belt to bodies of significantly varying size.

BRIEF DESCRIPTION OF THE DRAWINGS

The foregoing objects and advantages will be better understood as the following description proceeds, taken in conjunction with the accompanying illustrative drawings, in which:

FIG. 5 is a plan view of the underlying belt wrap assembly;

FIG. 6 is a view comparable to FIG. 5, showing the reverse side of the underlying wrap assembly;

FIG. 7 shows the wrap assembly in a rear plan view with the side pulls loose;

DESCRIPTION OF PREFERRED EMBODIMENTS

Figure 1:
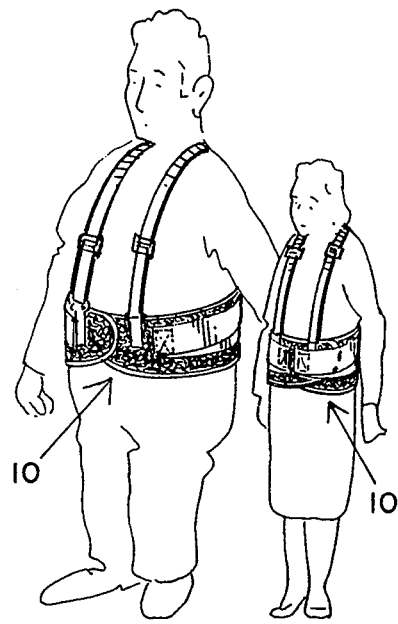
FIG. 1 is a view showing a large man and a small woman both wearing an adjustable lifting belt exemplary of the present invention.

The preferred embodiments of the present lifting belt are illustrated in their usage in FIG. 1. There it will be seen that the lifting belt assembly 10 is wrapped around a rather large man and the front two overlapping wrap end members secure the belt in place. Next to the large man is a small woman wearing the belt assembly 10 in which significantly greater overlaps appear in front, and the suspender adjustments are notably shortened. In this context the dimensions of the subject lifting belt assembly 10 become significant since they are developed to show proportion which make possible the wide adjustment which can be achieved.

Figure 2:
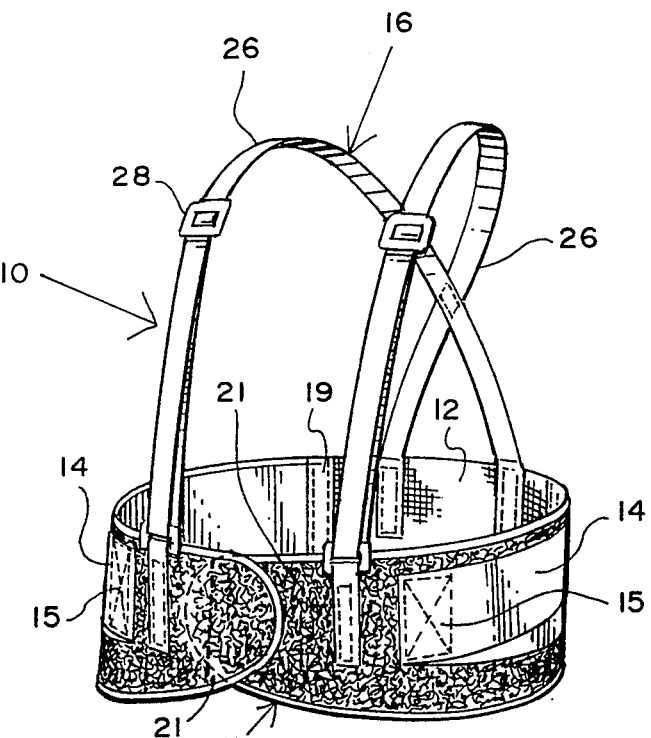
FIG. 2 shows the lifting belt worn by the large man with the overlapping adjustable portion shown in phantom adjusted for his girth and height.

The lifting belt 10 as shown in FIG. 2 includes the underlying non-expandable wrap assembly 11 and the expandable lumbar panel 12, and in the outer portion, the expandable side pull members 14. All of the elements of the belt are fastened together by a material known by the trademark Velcro. The Velcro has hook sides and a soft or locking side. In connection with the preferred embodiments, the hooks are shown in a curled configuration, and the locking portion in a softer wool-like configuration. In all instances, it should be remembered that the members may be reversed or, in the event releasable locking members of like configuration are employed, they are contemplated as well for the securement function.

Figure 3:
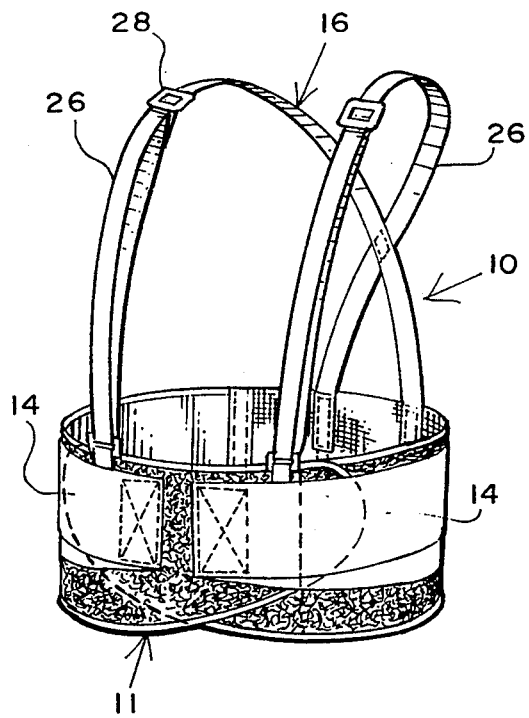
FIG. 3 is a view similar to that of FIG. 2, but in smaller scale, and illustrating with significantly more overlapping the adjusted belt for the small female shown in FIG. 1.

In FIG. 3 it will be seen that the suspender assembly 16 has been adjusted differently than shown in FIG. 2. The showing in FIG. 2 is comparable to the adjustment of the lifting belt 10 for the large man shown in FIG. 1. Conversely, the showing in FIG. 3 shows a significant overlap of the wrap assembly 11 and the expandable side pulls 14 much as appears on the woman in the right-hand portion of FIG. 1. In both applications as illustrated in FIGS. 2 and 3, the last securing step is to position the removably securable end portions 15 of the expandable side pulls 14 over the releasably securable exterior portion of the wrap assembly 11. Thus as shown in FIG. 2, the wrap assembly 11 barely overlaps where it is employed on a person with a large waist, whereas the wrap assembly 11 and elastic side pulls 14 have a very substantial overlap to accommodate a slender person.

Figure 4:
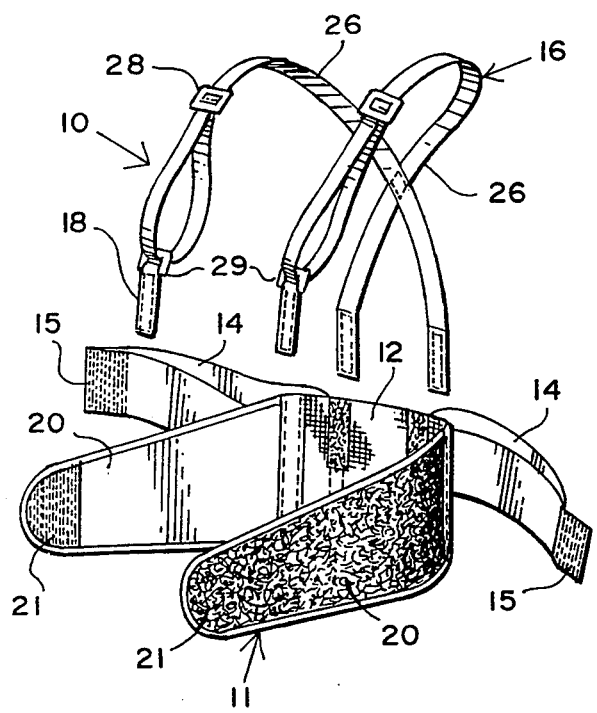
FIG. 4 is an exploded layout view of the belt showing its three major elements.

In FIG. 4 the suspender assembly and its securement to the wrap assembly 11 is more fully illustrated. Notably, each of the four suspender straps 26 have suspender securable ends 18 at their bottom portion, which ends 18 are secured by means of the end connectors 29. Buckles 28 are provided at the forward portion of the straps 26 in order to adjust for the space between the shoulder and the waist of the person wearing the belt.

Turning now to FIG. 5 it will be seen that the expandable lumbar panel 12 at the rear portion of the wrap assembly 11 includes stays 19 which are inserted in stay pockets 19'. As shown, four such stays are employed. The central two stays have a pair of suspender anchors 25 to which the lower portion of the suspenders are anchored. In this regard, it will be seen that the suspenders can extend well beneath the length of the lumbar panel anchors 25, and this in combination with shortening the suspender length through the buckles 28, achieve an adjustment of the entire suspender assembly 16 to accommodate the slender and smaller user.

The showing in FIG. 6 is the rear portion of the belt to where it will be seen that the expandable side pulls 14 are anchored to the center two back stays 19, and extend laterally to a position close to the wrap ends 21 of the wrap non-expandable wrap body portion 20. The locking wrap end 21 engages the front portion of the wrap ends 21 on the wrap surface 22 which, as will be noted, receives the locking members of the wrap ends 21, and the locking ends of the removable securing end portion 15. FIG. 7 shows the expandable side pulls 14 in their free or unsecured relationship to the wrap 20, and reveals that the preferred expandable side pulls 14 actually are a double overlapping elastomeric material with two sections 14, 14' as shown. The two sections are spread where they join the back stays 19 on the expandable lumbar panel 12, but taper to the single removable securing side pull end portion 15.

Figure 8:
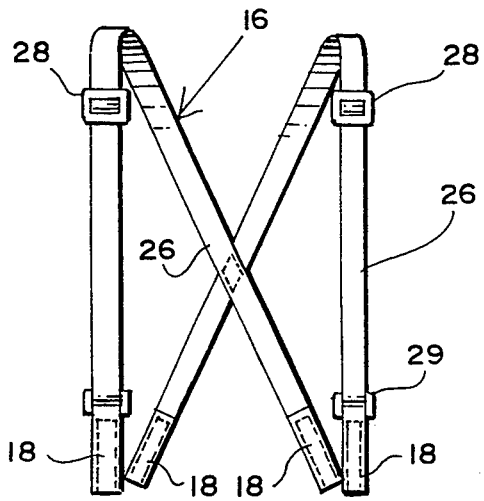
FIG. 8 is a plan view of the suspender assembly.
Figure 9:
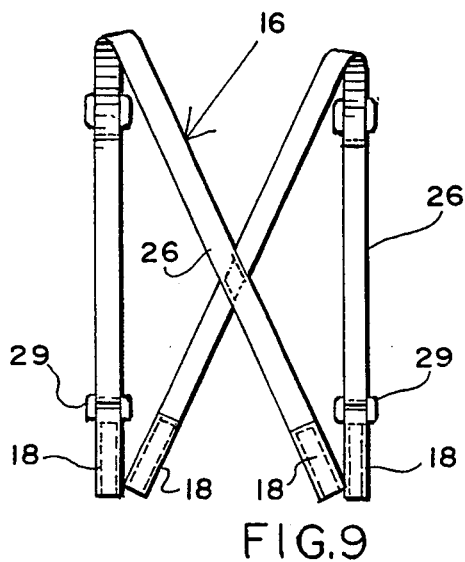
FIG. 9 is a reverse plan view of the suspender assembly.

The suspenders are shown in plan view both front and rear in FIGS. 8 and 9. There, as stated before, each of the strap ends has a suspender securing end 18 which is readily secured to the wrap assembly 11 by means of the securement of the ends 18. The securing ends 18 are coupled by means of the loop end connector 29 to the balance of the suspender straps 26. The adjustment to the distance between the shoulder and the waist is made by the buckles 28 which are traditional adjustments for suspenders and will be readily understood by any user.

Figures 10, 11:
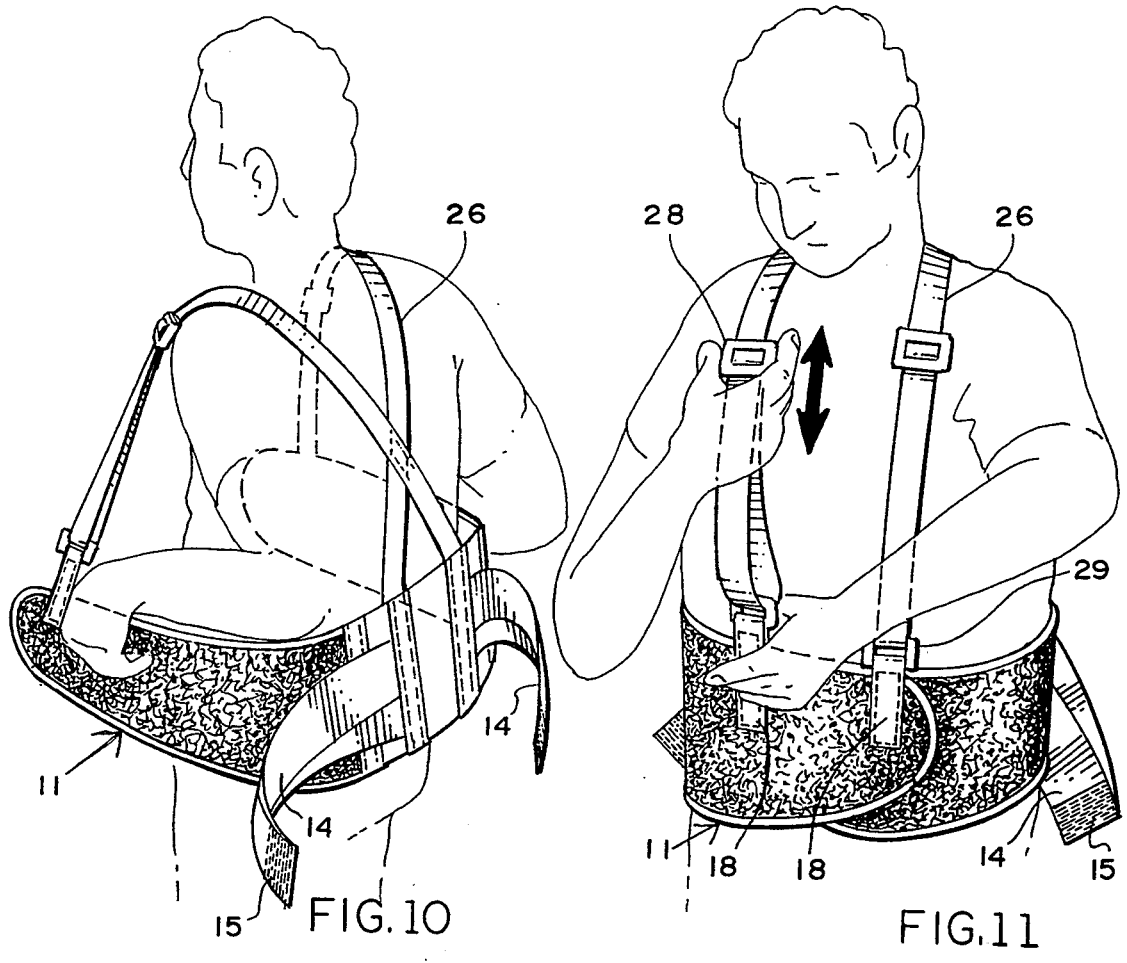
FIG. 10 illustrates the average-size man putting the belt on by slipping beneath the suspenders.
FIG. 11 is a sequential view from FIG. 10 above illustrating how the suspenders are adjusted both top and bottom.
Figures 12, 13:
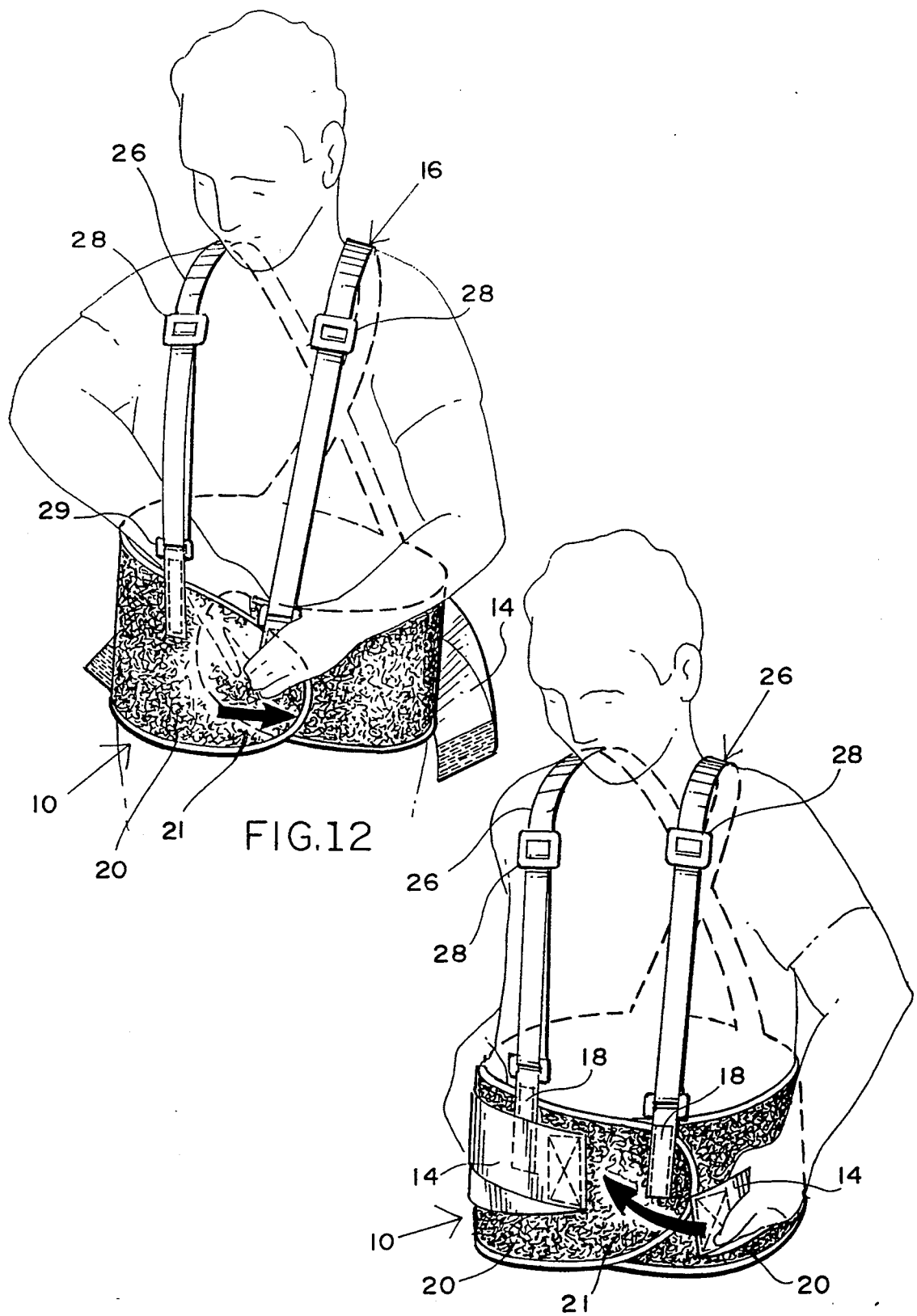
FIG. 12 is a sequential view from FIG. 11 following the adjustment of the suspenders showing the adjustment of the main underlying wrap assembly.
FIG. 13 is the final sequential after FIG. 12 view showing the application of the elastic side pulls to the underlying wrap assembly.

Applying the belt assembly to a user is illustrated sequentially in FIGS. 10–13. Initially the suspender straps 26 are passed over the shoulders, and then the wrap assembly 11 is secured around the waist. At this point the expandable side pulls 14 are left positioned to the wrap assembly in a non-expanded state, but in a ready position for securement when the wearer prepares to lift a load. FIG. 11 illustrates how the suspender assembly 16 is adjusted by both the adjustable buckles, and the positioning of the suspender securing ends 18 on the wrap assembly 11. Thereafter, as shown in FIG. 12, with the suspenders secured in place, the wrap assembly 11 is secured by attaching the wrap end 21 to the outer face of the adjacent wrap end.

Finally, as a load lifting is anticipated, the last step is shown in FIG. 13 where the expandable side pulls 14 are stretched in place and lockingly secured to the wrap assembly 11 which is beneath the side pulls. Here it will be further seen that the suspender anchors or securable ends 18 are beneath the side pulls.

The belt 10 is made out of 150 Denier polyester and releasably securable elastic basically 66% polyester and 34% Bared EX. The belt is 150 Denier polyester elastic of which the lumbar panel is a part. The side pulls are also 150 Denier polyester elastic. The releasably securable material is generally sold under the trademark Velcro. The hook and wooly portions are applied in opposite positions as shown throughout this description. Where possible, poly cotton binding which is inelastic is secured to the lateral edges of the non-expandable wrap edges 20.

In addition, as to dimensions, the overall dimension from one end to the other of the non-expandable wrap 20 is approximately forty-eight inches. The height of the lumbar panel 12 is approximately nine inches, and the width of the lumbar panel 12 is approximately thirteen inches. The expandable side pulls 14 extend approximately fourteen inches in the unexpanded mode from the central of the two stay pockets 19'. The suspender back straps extend downwardly approximately nine inches from the intersection in the rear, and the suspender securable ends 18 extend an approximate additional four inches. At the other end, the strap extends from the back intersection approximately thirty-six inches when fully let out. By using the adjustable loop buckles 28, this distance can be shortened significantly for the smaller user.

Although particular embodiments of the invention have been shown and described in full here, there is no intention to thereby limit the invention to the details of such embodiments. On the contrary, the intention is to cover all modifications, alternatives, embodiments, usages and equivalents as fall within the spirit and scope of the present invention, specification and appended claims.

What is claimed is:

1. A lifting belt for adjustable sizing to various sized users, both males and females, comprising, in combination,
   an underlying wrap assembly having a central expandable lumbar panel with lateral edges with vertical stays and wrap around portions each extending from the lumbar panel lateral edges to an end with removably securable faces,
   one of said ends having a reversed removably secured closure portion,
   said underlying wrap assembly outer surface comprising a removable material extending from the lumbar panel edges to the ends,
   suspenders having four ends, two front and two rear, to secure to the underlying wrap assembly,
   two suspender anchors central of the underlying wrap assembly lumbar panel oriented vertically with removable securable material,
   said belt having two elastic side pull portions extending from the point where they are secured to the lumbar expandable panel lateral edges,
   and removable securable end tabs on said side pulls for removably securing to the outer face of the underlying wrap assembly outer surface.

2. A method for securing a load belt to a user, which load belt has an underlying wrap assembly with a central expandable lumbar panel and end overlapping closures with removable securable material on the front face extending to the ends and a single removable secured lock on the underneath portion of one of said ends; suspenders with four removably secured ends to secure to the underlying wrap assembly on back and front portions thereof, and elastic side pulls secured to the lumbar panel of the underlying belt and extending forwardly and terminating in a removably securable material on the underneath portion for engaging the removable securable material on the underlying overlapping wrap assembly of the underlying wrap comprising the steps of removably securing the suspenders to the underlying wrap and adjusting the same at the two locations at the back, and at the two locations on the front temporarily, passing the suspenders over the shoulders of the user and then temporarily securing the ends of the underlying wrap in overlapping comfortable relationship, thereafter securing the ends of the front portion of the suspenders at a location on the wrap ends, and thereafter closing the elastic side pulls prior to lifting engagement by the user.

3. A lifting belt for adjustable sizing to various sized users, both males and females, comprising, in combination, an underlying wrap assembly having a rearward central expandable lumbar panel with vertical lateral edges with vertical stays and wrap around portions each extending from the lumbar panel lateral edges to an end, one of said ends having a reversed removably secured closure portion, said wrap assembly outer surface comprising a removably securable material, suspenders having ends with removably securable portions to secure to the underlying wrap assembly outer surface, suspender anchor portions central of the underlying wrap lumbar panel oriented vertically with removable securable material, said belt having opposed elastic side pull portions extending from the point where they are secured to the back of the lumbar panel, and removable securable end tabs on said side pulls for removably securing to the outer face of the underlying wrap assembly outer surface portions to the underlying belt.

4. In the belt of claim 3,
said side pulls each having two strap portions.

5. In the belt of claim 3,
said side pulls being secured to the wrap at the lateral edges of the lumber panel.

6. A method for securing a load belt to a user, which load belt has an underlying wrap assembly with a central expandable lumbar panel and end overlapping closures with removable securable material on the front face and a single removable secured lock on the underneath portion of one of said ends; suspenders with removably secured ends to secure to the underlying wrap assembly at rear and forward portions of the wrap assembly, and elastic side pulls secured to the lumbar panel of the underlying belt and extending forwardly and terminating in a removably securable material on the underneath portion for engaging and removable securable material on the underlying overlapping wrap assembly of the underlying wrap comprising the steps of removably securing the suspenders to the underlying wrap portion thereof and adjusting the same at locations the rear vertically, and at the forward locations temporarily, passing the suspenders over the shoulders of the user and then temporarily securing the ends of the underlying wrap in overlapping comfortable relationship, then securing the ends of the forward portion of the suspenders at a location on the wrap ends, and thereafter closing the elastic side pulls prior to lifting engagement by the user.

7. A lifting belt for adjustable sizing to various sized users, both males and females, comprising, in combination, an underlying wrap assembly having a central expandable lumbar panel with spaced lateral edges and vertical stays and wrap around portions each extending from the lumbar panel edges to an end with removably securable faces, one of said ends having a reversed removably secured closure portion, said wrap assembly outer surface comprising a removable securable material, suspenders having ends, front and rear, to secure to the underlying wrap, a suspender anchor member on the underlying belt lumbar panel, wrap ends which are secured to the lumbar panel, said belt having opposed elastic side pull portions extending from the point where they are secured to the wrap, and removable securable end tabs on said side pulls for removably securing to the outer face of the wrap portions to the underlying belt.

8. A lifting belt and suspender combination for adjustable sizing to various sized users, both males and females, comprising, in combination, an underlying wrap assembly having a central rear expandable lumbar panel and wrap around portions each extending from the lumbar panel to an end with removably securable faces, one of said ends having a reversed removably secured closure portion, said wrap assembly outer surface comprising a removable securable material, suspenders having four ends each with a removably secured face, two front and two rear, to secure to the underlying wrap, two suspender anchors central of the underlying belt lumbar panel oriented vertically with removable securable material, said wrap having two elastic side pull portions extending from the point where they are secured toward the lumbar panel, and removable securable end tabs on said side pulls for removably securing to the outer face of the wrap portions to the underlying wrap and over the two suspender front ends.

* * * * *